US012807996B2

(12) United States Patent
Sun et al.

(10) Patent No.: US 12,807,996 B2
(45) Date of Patent: Nov. 24, 2026

(54) CHROMATIN MAPPING ASSAYS AND KITS USING LONG-READ SEQUENCING

(71) Applicant: EPICYPHER, INC., Durham, NC (US)

(72) Inventors: Zu-Wen Sun, Brentwood, TN (US); Martis W. Cowles, Chapel Hill, NC (US); Michael-Christopher Keogh, Cambridge, MA (US); Ellen N. Weinzapfel, Durham, NC (US)

(73) Assignee: EpiCypher, Inc., Durham, NC (US)

( * ) Notice: Subject to any disclaimer, the term of this patent is extended or adjusted under 35 U.S.C. 154(b) by 1294 days.

(21) Appl. No.: 17/429,729

(22) PCT Filed: Feb. 11, 2020

(86) PCT No.: PCT/US2020/017597

§ 371 (c)(1),
(2) Date: Aug. 10, 2021

(87) PCT Pub. No.: WO2020/167712

PCT Pub. Date: Aug. 20, 2020

(65) Prior Publication Data

US 2022/0049311 A1 Feb. 17, 2022

Related U.S. Application Data

(60) Provisional application No. 62/803,829, filed on Feb. 11, 2019.

(51) Int. Cl.

*C12Q 1/6883* (2018.01)
*C12Q 1/6804* (2018.01)
*C12Q 1/6806* (2018.01)

(52) U.S. Cl.

CPC ......... *C12Q 1/6883* (2013.01); *C12Q 1/6806* (2013.01); *C12Q 1/6804* (2013.01);
(Continued)

(58) Field of Classification Search

None
See application file for complete search history.

(56) References Cited

U.S. PATENT DOCUMENTS

2015/0111788 A1 4/2015 Fernandez et al.
2016/0060691 A1 3/2016 Giresi et al.
(Continued)

FOREIGN PATENT DOCUMENTS

JP 2018532373 A 11/2018
WO 2014165549 A1 10/2014
(Continued)

OTHER PUBLICATIONS

Risca et al. (Variable chromatin structure revealed by in situ spatially correlated DNA cleavage mapping, Nature, published 2017). (Year: 2017).*

(Continued)

*Primary Examiner* — Heather Calamita
*Assistant Examiner* — Elizabeth Rose Lafave
(74) *Attorney, Agent, or Firm* — Myers Bigel, P.A.

(57) ABSTRACT

This present invention relates to methods for carrying out chromatin mapping assays that use enzymes to incorporate barcoded DNA at targeted genomic regions followed by long-read sequencing (e.g., Third Generation Sequencing (TGS)). This approach enables the mapping of chromatin targets using TGS and can be used for a wide range of elements or features, including histone post-translational modifications, chromatin associated proteins, nucleosome positioning, and chromatin accessibility. The invention further relates to kits and reagents for carrying out the methods on chromatin samples that include one or more cells.

20 Claims, 4 Drawing Sheets

(52) U.S. Cl.
CPC . *C12Q 2521/125* (2013.01); *C12Q 2521/301* (2013.01); *C12Q 2521/507* (2013.01); *C12Q 2525/191* (2013.01); *C12Q 2531/113* (2013.01); *C12Q 2535/122* (2013.01); *C12Q 2563/179* (2013.01); *C12Q 2600/154* (2013.01)

(56) References Cited

U.S. PATENT DOCUMENTS

| | | | |
|---|---|---|---|
| 2016/0208323 | A1 | 7/2016 | Bernstein et al. |
| 2018/0340169 | A1 | 11/2018 | Belhocine et al. |

FOREIGN PATENT DOCUMENTS

| | | | | |
|---|---|---|---|---|
| WO | 2015179706 A1 | 11/2015 | | |
| WO | 2017025594 A1 | 2/2017 | | |
| WO | WO-2018064208 A1 * | 4/2018 | ......... | C12N 15/1034 |
| WO | 2019169114 A1 | 9/2019 | | |

OTHER PUBLICATIONS

Huda et al. (Epigenetic histone modifications of human transposable elements: genome defense versus exaptation, Mobile DNA, published Jan. 2010) (Year: 2010).*
Yen et al. ("Transposase mapping identifies the genomic targets of BAP1 in uveal melanoma", BMC Medical Genomics, published Nov. 2018) (Year: 2018).*
Yant et al. ("Site-directed transposon integration in human cells", Nucleic Acids Research, published Mar. 7, 2007) (Year: 2007).*
"Extended European Search Report corresponding to European Application No. 20755712.5 dated Oct. 19, 2022".
Kaya-Okur, Hatice S, et al., "CUT & Tag for efficient epigenomic profiling of small samples and single cells", Nature Communications 10(1):1-10 (Apr. 29, 2019).
Perera, Rukshan T, et al., "Detection of benzo[a]pyrene-guanine adducts in single-stranded DNA using the alpha-hemolysin nanopore", Nanotechnology 26(7):74002 (Jan. 28, 2015) 7 pages.
Wang, Yunhao , et al., "Single-molecule long-read sequencing reveals the chromatin basis of gene expression", Genome Research 29(8):1329-1342 (Jun. 14, 2019).
"International Search Report and Written Opinion corresponding to International Application No. PCT/2020/017597 mailed Jun. 10, 2020".
"International Preliminary Report on Patentability corresponding to International Application No. PCT/US2020/017597 mailed Aug. 26, 2021".

* cited by examiner

CHROMATIN MAPPING ASSAYS AND KITS USING LONG-READ SEQUENCING

STATEMENT OF PRIORITY

This application is a 35 U.S.C. § 371 national phase application of PCT Application PCT/US2020/017597, filed on Feb. 11, 2020, which claims the benefit of U.S. Provisional Application Ser. No. 62/803,829, filed Feb. 11, 2019, the entire contents of each of which are incorporated by reference herein.

FIELD OF INVENTION

This present invention relates to methods for carrying out chromatin mapping assays that use enzymes to incorporate barcoded DNA at targeted genomic regions followed by long-read sequencing (e.g., Third Generation Sequencing (TGS)). This approach enables the mapping of chromatin targets using TGS and can be used for a wide range of elements or features, including histone post-translational modifications, chromatin associated proteins, nucleosome positioning, and chromatin accessibility. The invention further relates to kits and reagents for carrying out the methods on chromatin samples that include one or more cells.

BACKGROUND OF INVENTION

Genomic mapping assays are widely used to study chromatin structure and function. These include assays that analyze genomic location and abundance of chromatin modifications, chromatin associated proteins (ChAPs), chromatin accessibility, and nucleosome positioning. Chromatin modifications include those that are added to residues on histone proteins or DNA. Histones residues on nucleosomes can be post-translationally modified (PTM) with a variety of chemical moieties, including lysine methylation, lysine acylation, arginine methylation, serine phosphorylation, etc., whereas DNA residues are modified with a number of different methylation variants (e.g., 5-methylcytosine, 5-hydrozxymethylcytosine, 5-formylcytosine, etc.). ChAPs include any protein that directly interacts with chromatin, including transcription factors that bind directly to DNA and "reader" proteins and enzymes that interact with or modify histone and/or DNA. ChAPs also include proteins that indirectly interact with chromatin via interactions with macromolecular complexes that regulate chromatin function, such as transcriptional regulation and chromatin remodeling complexes. Genomic regions devoid of nucleosomes are associated with gene transcription and activation as these chromatin regions are "accessible" to transcriptional machinery, whereas genomic regions of high nucleosome density are generally correlated with gene inactivation.

Histone modifications and ChAPs are routinely mapped genome-wide using chromatin immunoprecipitation followed by next-generation sequencing (ChIP-seq). Of note, alternative chromatin mapping methods have been developed beyond ChIP, including those that tether enzymes to genomic regions, resulting in release, enrichment, and subsequent analysis of target material (e.g., DamID, ChIC, ChEC, CUT&RUN, and CUT&Tag) [1-3]. For example, the related ChIC (Chromatin ImmunoCleavage [4,5]) and CUT&RUN (Cleavage Under Targets & Release Using Nuclease) methods use a PTM- or factor-specific antibody to tether a fusion of protein A and protein G-Micrococcal Nuclease (pAG-MNase) to genomic binding sites in intact cells or extracted nuclei, which is then activated by calcium addition to cleave DNA. PAG-MNase provides a cleavage tethering system for antibodies to any PTM or ChAP. The CUT&RUN protocol has been streamlined (vs. ChIC) by using a solid support (e.g., lectin-coated magnetic beads) to adhere cells (or nuclei). Similarly, CUT&Tag uses protein A tethered to a hyperactive transposase (pA-Tn5), followed by controlled activation of Tn5 to deliver sequencing adaptors for paired-end sequencing. This method is ultrasensitive and fast by removing the library preparation step, providing a tractable approach for chromatin mapping of select targets from single cells [6].

There are several commercially available assays for genome-wide analysis of chromatin accessibility. Early assays used DNase I followed by sequencing (DNase-Seq) to identify nucleosome depleted regions genome-wide (termed DNase I hypersensitivity sites; DHSs) [7,8]. A related approach using micrococcal nuclease I (MNase I) has also been developed to map nucleosome positioning [9], the inverse of chromatin accessibility. While these approaches work with both native (i.e., unfixed) and fixed cells, they require extensive enzyme optimization and high cell requirements. Recent advances to the DNase I protocol have enabled lower cell requirements with DHS mapping using a single cell; however, DHSs mapped to <2% of the reference genome, significantly limiting its utility [10]. FAIRE-seq (formaldehyde assisted isolation of regulator element sequencing) is a highly sensitive approach to enrich nucleosome-depleted regions, but as the name suggests, it requires formaldehyde fixation [11]. ATAC-seq uses a Tn5 transposase that preferentially targets and delivers its sequencing adaptor payload into accessible chromatin vs. inaccessible regions [12]. This method is quickly garnering adoption in the field due to its ease, speed, and low cell requirements. Indeed, ATAC-seq assays can be performed in a single day, demonstrating the potential use of this approach for clinical applications [13].

The application of hyperactive transposases in chromatin mapping assays (e.g., CUT&Tag and ATAC-seq) has dramatically improved assay throughput and increased assay sensitivity. In these assays, the transposon is activated in vitro containing engineered DNA barcodes, which can be subsequently amplified using PCR and analyzed using massively parallel second-generation sequencing [13]. Native transposons encode the transposase gene flanked by two 19 bp sequences that are activated for genome targeting by interactions with the transposase protein (FIG. 1A). Current genomic assays (e.g., ATAC-seq, CUT&Tag) use modified transposons that lack an internal DNA region linking the activated transposase-bound DNA oligos, resulting in double-strand breaks and the release of DNA fragments after chromatin targeting (FIG. 1B) [13]. This modification is advantageous for massive parallel second-generation sequencing as it breaks chromatin into smaller DNA fragments. See FIG. 2 for an example of a typical CUT&Tag workflow.

Third Generation Sequencing (TGS) platforms generate long reads from native DNA at relatively low cost, facilitating novel applications that are inaccessible by standard approaches. TGS platforms, such as OXFORD NANOPORE TECHNOLOGIES® (ONT) and Pacific BioSciences® (PacBio), are radically altering the field of genomics research, increasing sequencing technology accessibility and providing crucial insights into human disease [14]. In nanopore sequencing, long fragments of DNA are passed through nanopores, which use changes in electrical impulses to denote different DNA nucleotides [14]. The use of long fragments of DNA is unique to TGS platforms, and enables mapping to repetitive regions and complex DNA sequences [14, 15]. Indeed, the OXFORD NANOPORE TECHNOLOGIES® nanopore sequencers can generate reads >1 Mb [16], and have been used to detect structural variants in breast and pancreatic cancer [18]. Recent studies have also applied nanopore sequencing to transcriptome profiling of mouse B-lymphocytes at single-cell resolution [19, 20], demonstrating the potential application of TGS to ultra-low cell inputs. Importantly, because there is no required PCR amplification step, TGS enables the direct detection of unique base modifications, including DNA methylation (5mC), which has been challenging to directly measure using standard second generation sequencing (FIG. 4, left panel) [21, 22]. These rich datasets enable "multiomic" analyses (e.g., DNA sequence variation in combination with 5mC), which have helped delineate distinct types of brain tumors [23]. Combined with the reduced costs, improved coverage, and real-time sequencing capabilities [23-26], TGS is redefining the boundaries of modern genomics research. However, this approach is not suitable for most chromatin mapping studies, which result in fragmentation of chromatin and thus are best suited for second-generation sequencing. New methods are needed to enable chromatin mapping studies that preserve sample integrity and are suitable for TGS. Such advances will provide low-cost sequencing solutions as well as novel multiomic analyses that include DNA methylation and chromatin profiling analysis. Further, use of TGS for single cell applications may result in increased genomic coverage per cell, a major limitation of current SGS-based single cell assays [22].

SUMMARY OF THE INVENTION

Current chromatin mapping assays known in the art result in chromatin fragmentation during sample processing (e.g., ChIP-seq, ATAC-seq, CUT&Tag, etc.), making them well suited for short-read second-generation sequencing (SGS). As such, current methods are not compatible with TGS, with the exception of DNA methylation [27]. New mapping methods that maintain chromatin integrity (i.e., are non-destructive) would be amenable to the mapping of chromatin elements (e.g., histone PTMs, ChAPs, nucleosome positioning, and chromatin accessibility) by TGS. These assays will have significant advantages over current SGS approaches, including increased access to chromatin mapping assays without the need for costly second-generation sequencing machines (e.g., nanopore sequencers), no PCR bias, and next-generation multiomic analysis, e.g., integration of DNA methylation with other genomic features, such as histone PTMs, ChAPs, and chromatin accessibility.

The present invention relates to novel methods for chromatin mapping assays using TGS. The approach uses enzymes to modify DNA by non-destructive means to include a unique molecular identifier that can be used to determine the location of a genomic element as well as sample multiplexing for bulk (i.e., more than one cell) or single cell analysis. The resulting chromatin sample can then be processed for TGS, such as nanopore or single molecule real time sequencing, wherein the location of genomic elements (e.g., histone PTMs, ChAPs, nucleosome position, chromatin accessibility, etc.) are mapped via the selective integration of barcoded DNA into sample chromatin. Samples may be sequenced using PCR-amplified chromatin or native chromatin. Sample genomic DNA may come from a single or multiple cells and be analyzed individually or multiplexed by pooling samples, each demarked by a unique DNA barcode, prior to whole genome sequencing. The methods described here may be used in any genome-wide assay known in the art which uses enzymes for chromatin mapping studies, including but not limited to ATAC-seq [13], CUT&Tag [6], and ChIL-seq [28]. This approach will result in long-sequencing reads, which results in better sequence coverage in areas of the genome that are challenging to map, such as repetitive regions. Long-reads will also result in greater sequencing coverage when input chromatin is limiting, such as single cell applications; these samples may be PCR amplified to increase chromatin input prior to sequencing. Further, TGS enables the use of native samples, which contain DNA modifications, that can be directly measured using TGS. This enables multiomic analyses, wherein DNA methylation is assessed in the context of other genomic elements, such as histone PTMs or chromatin accessibility; these samples would not be PCR amplified to preserve native DNA modifications. Of note, DNA methylation information is typically lost in current SGS-based approaches following PCR amplification.

In some embodiments, a modified Tn5 can used to map chromatin accessibility. In these assays, the canonical function of the Tn5 enzyme are leveraged, loading the hyperactive Tn5 with a transposon carrying a unique identifier sequence, to insert its DNA-barcoded payload at open chromatin. Following insertion, DNA is repaired using molecular biology techniques known in the art (e.g., a combined treatment with T4 DNA polymerase and T4 DNA ligase (as done previously [28]) and sequenced using TGS (e.g., PacBio or nanopore). Finally, the insertion of barcoded DNA is used to map the chromatin loci with high accessibility (similar to ATAC-seq) and can be used to analyze one or more cells in a single assay. In some embodiments, a library of Tn5 transposons is assembled, each denoted by a unique DNA barcode. This library can be used to treat various bulk samples (i.e., more than one cell), which can then be pooled, sequenced, and deconvolved using their unique DNA barcode (i.e., multiplex analysis). This library can also be used for single cell analysis using a combinatorial indexing approach [29], wherein the assay is performed on a population of cells, which are then split into a multi-well plate (e.g., 96-, 384-, 1536-well) containing ~20 cells per well. Each well is then processed for native chromatin sequencing using adaptors that include a second barcode or PCR amplified using primers that include a second barcode and sequenced using TGS. This approach provides a double barcode signature that can be used to assign reads to a specific single cell (SC). In some embodiments, assays can be deployed using single cell droplet-based methods, such as those commercially available by 10× genomics or BIO-RAD®. In some embodiments, native chromatin is sequenced. These assays may be used to perform multiomic analyses wherein DNA modifications are analyzed in concert with chromatin accessibility. In some embodiments, samples are PCR-amplified prior to sequencing. In some embodiments, other enzymes that modify chromatin are used in place of Tn5, such as integrases or DNA methyltransferases.

In some embodiments, a modified Tn5 can be used to map histone PTMs, ChAPs, or nucleosome positioning (e.g., pAG-Tn5). In these assays, the canonical function of the Tn5 enzyme is leveraged, loading the hyperactive Tn5 with a transposon carrying a unique identifier sequence to insert its DNA-barcoded payload. Unlike the modified Tn5 used for chromatin accessibility mapping, this modified Tn5 is fused to an antibody binding moiety to enable antibody-targeting (a modified version of pAG-Tn5 as used in CUT&Tag [pAG-mTn5]). Antibodies used in this assay can target any chromatin element or binding protein, such as histone PTMs, nucleosomes, ChAPs, and DNA methylation. Following insertion, DNA is repaired using molecular biology techniques known in the art (e.g., a combined treatment with T4 DNA polymerase and T4 DNA ligase as done previously [28]) and sequenced using TGS (e.g., nanopore or single molecule real time sequencing). Finally, the insertion of barcoded DNA is used to map antibody targeted chromatin regions, generating chromatin maps similar to CUT&Tag and can be used to analyze one or more cells in a single assay. See FIG. 4 for an example workflow of how the modified pAG-Tn5 (pAG-mTn5) can be used to integrate a barcode into chromatin, followed by DNA repair and TGS. Tn5 can be fused to any protein binding moiety, such as Protein A, Protein G, Biotin, GST, etc. In some embodiments, a library of pAG-mTn5 transposons is assembled, each denoted by a unique DNA barcode. This library can be used to treat various bulk samples (i.e., more than one cell), which can then be pooled, sequenced, and data can be deconvolved using each samples DNA barcode (i.e., multiplex analysis). DNA barcodes are used to indicate genomic regions where the antibody targeted, such as a PTM or ChAP. This library can also be used for single cell analysis using a combinatorial indexing approach [29], wherein the assay is performed on a population of cells, which are then split into a multi-well plate (e.g., 96-, 384-, 1536-well) containing ~20 cells per well. Each well is then PCR amplified using primers that contain a second barcode (i.e., molecular identifier) and are sequenced using TGS. This approach provides a double barcode signature that can be used to assign reads to a specific SC. In some embodiments, assays can be deployed using single cell droplet-based methods, such as those commercially available by 10× genomics or BIO-RAD®. In some embodiments, native chromatin is sequenced. These assays may be used to perform multiomic analyses wherein DNA modifications are analyzed in concert with other chromatin features (e.g., histone PTMs or ChAPs). In some embodiments, samples are PCR-amplified prior to sequencing, which may be useful for low cell input or single cell applications. In some embodiments, other enzymes that modify chromatin are used in place of Tn5, such as integrases or DNA methyltransferases.

Thus, one aspect of the invention relates to a synthetic transposon comprising a DNA barcode region linked on its 5' and 3' end to a flanking region that is recognized by a transposase, wherein the synthetic transposon does not encode a transposase.

Another aspect of the invention relates to a transposome comprising the synthetic transposon of the invention and a transposase bound to each of the terminal inverted repeats.

A further aspect of the invention relates to a library comprising two or more of the synthetic transposons of the invention and/or two or more of the transposomes of the invention, wherein each synthetic transposon comprises a unique DNA barcode.

An additional aspect of the invention relates to a kit comprising the synthetic transposon, transposome, or the library of the invention.

Another aspect of the invention relates to a method for chromatin mapping, comprising:

a) targeting an enzyme to a specific feature in chromatin in a sample;
b) activating the enzyme to alter or label DNA local to the feature;
c) preparing the chromatin for sequencing;
d) sequencing the chromatin using long-read sequencing; and
e) mapping the location of the chromatin feature based on the locations of altered or labeled DNA.

In some embodiments, the methods may be used to map chromatin accessibility. In some embodiments, the methods may be used to map chromatin modifications, chromatin-associated proteins, or nucleosome positioning. In some embodiments, the methods are part of multiomics assays.

In some embodiments, the methods of the invention may further comprise steps of using the sequencing results to compare chromatin features between healthy and disease tissues, predict a disease state, monitor response to therapy, and/or analyze tumor heterogeneity.

These and other aspects of the invention are set forth in more detail in the description of the invention below.

DETAILED DESCRIPTION OF THE INVENTION

Figure 1A:
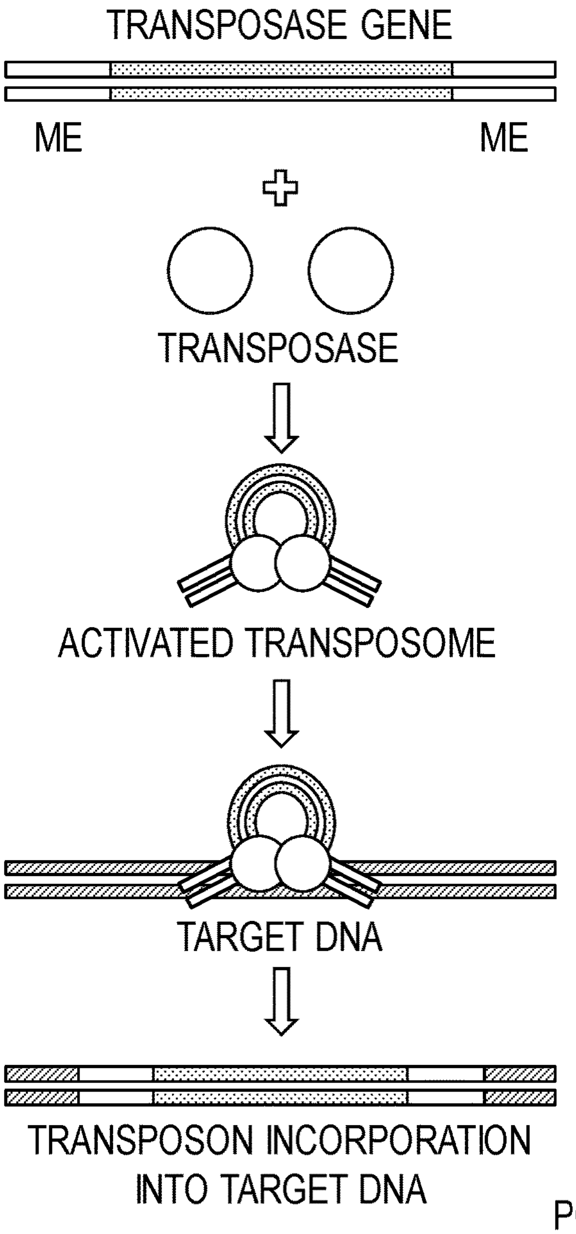
FIGS. 1A-1B show transposon schematics. (A) A cartoon showing sequence layout of native transposase, with transposase gene flanked by defined ends. This transposon DNA sequence interacts with the transposase enzyme to create an activated transposome, which can then target and deliver its payload into target DNA. (B) Cartoon showing mutated hyperactive transposome (e.g., Tn5) used in ATAC-seq. This hyperactive transposome lacks the transposon gene, which causes chromatin to fragment following transposition. This process has been termed tagmentation. The resulting DNA fragments can then be PCR amplified and sequenced using massive parallel sequencing (i.e., second-generation sequencing).
Figure 1B:
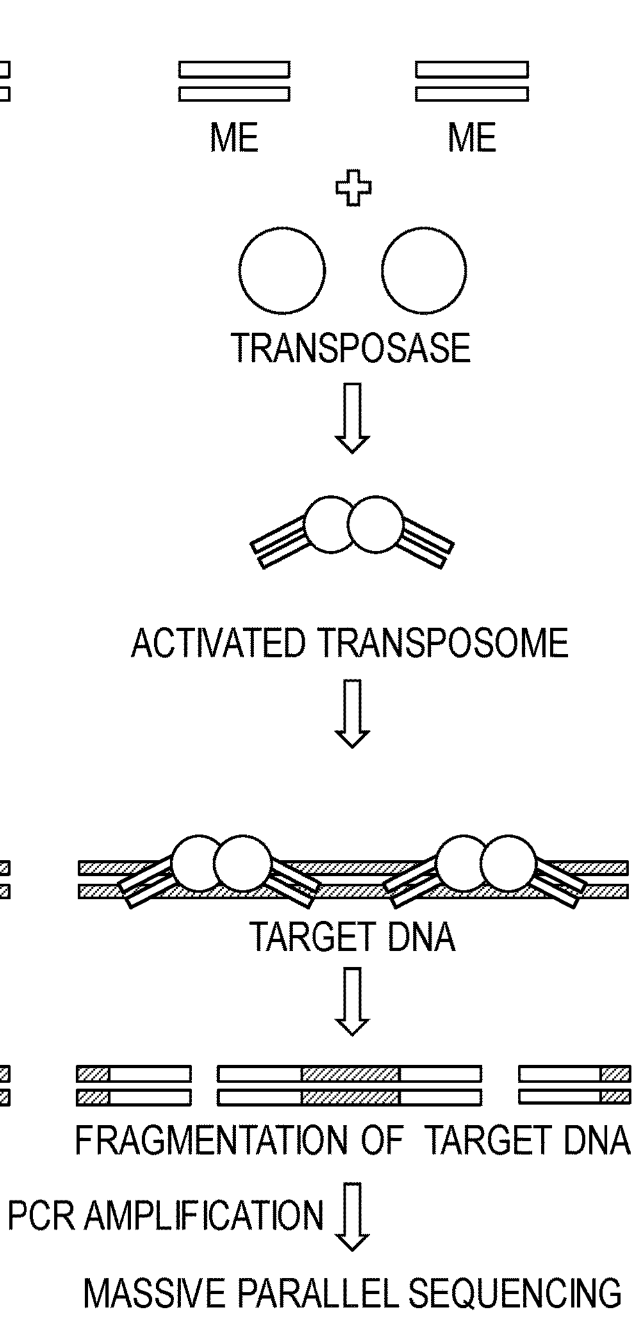
Figure 2:
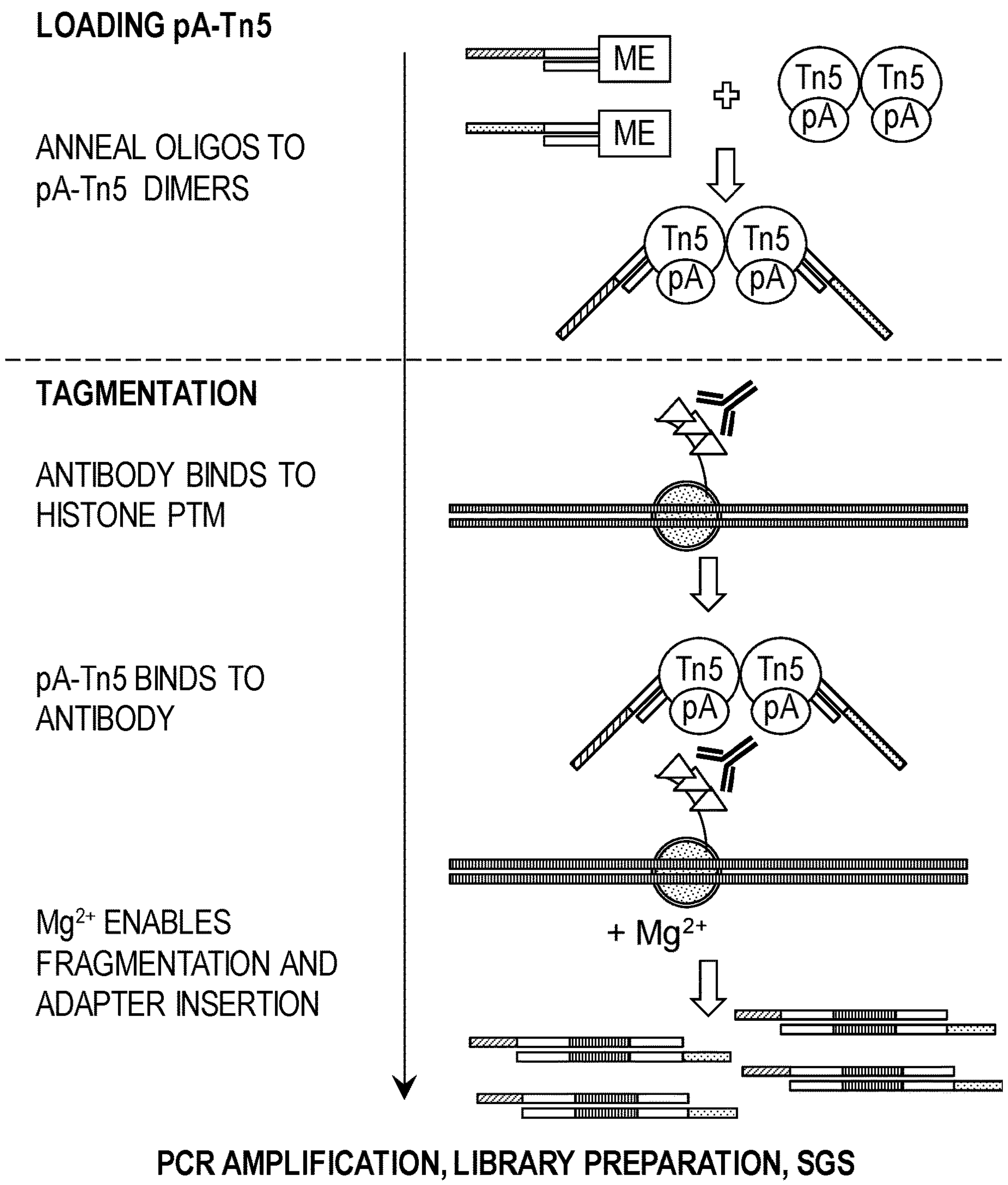
FIG. 2 shows a summary of the CUT&Tag protocol as described in [6].
Figure 3:
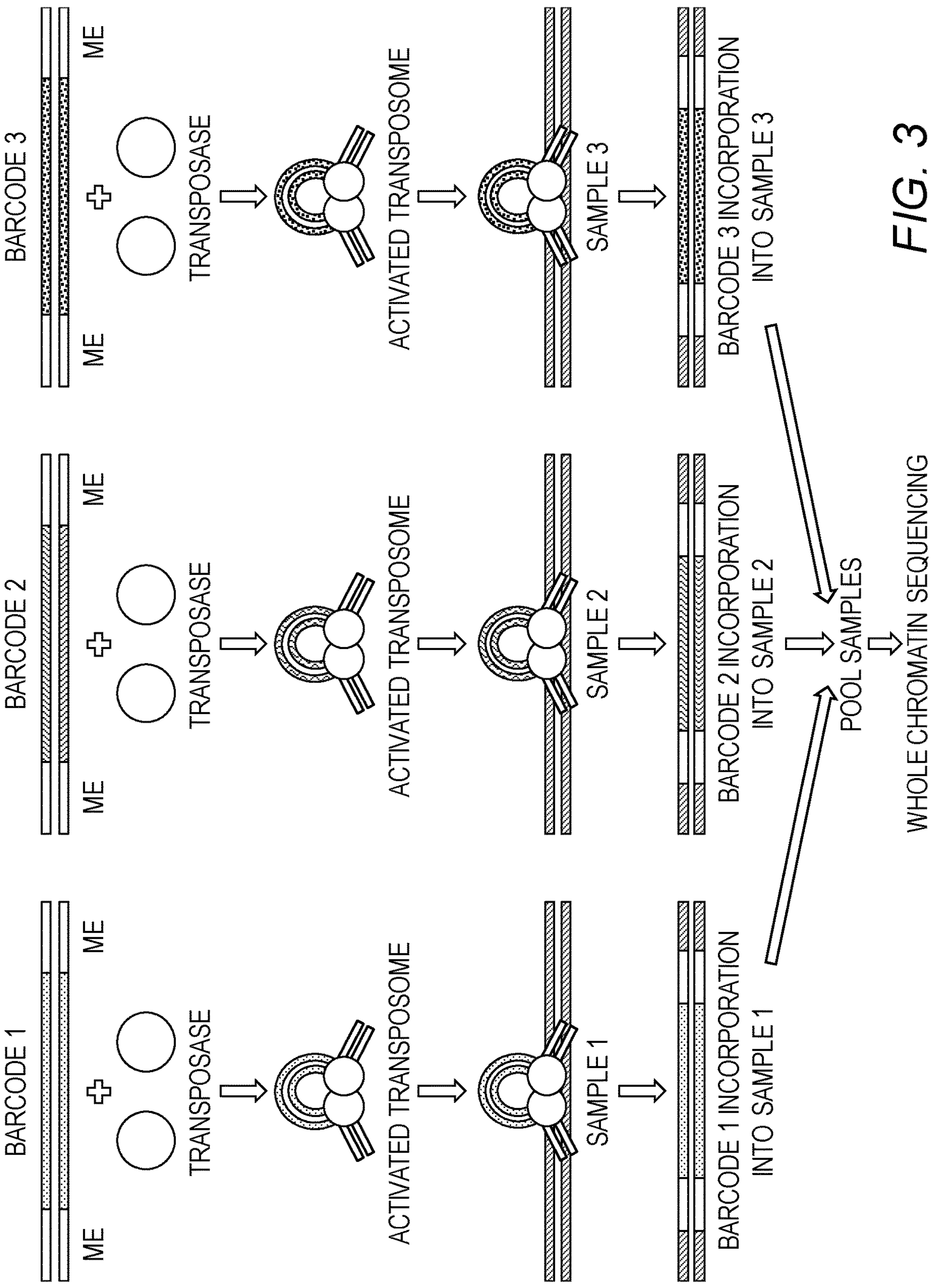
FIG. 3 shows a schematic of the invention. Transposons are modified to contain an internal identified sequence (i.e., barcode) in place of the transposase gene. This allows the payload to be incorporated into target DNA and importantly does not result in sequence fragmentation. This method can be performed on multiple samples, which are then pooled and processed for whole chromatin sequencing. The incorporated DNA sequence can be used for chromatin mapping and distinguish samples when multiplexing. This method can also be used for single cell analysis using various split and pool strategies, similar to those previously described [29, 30].
Figure 4:
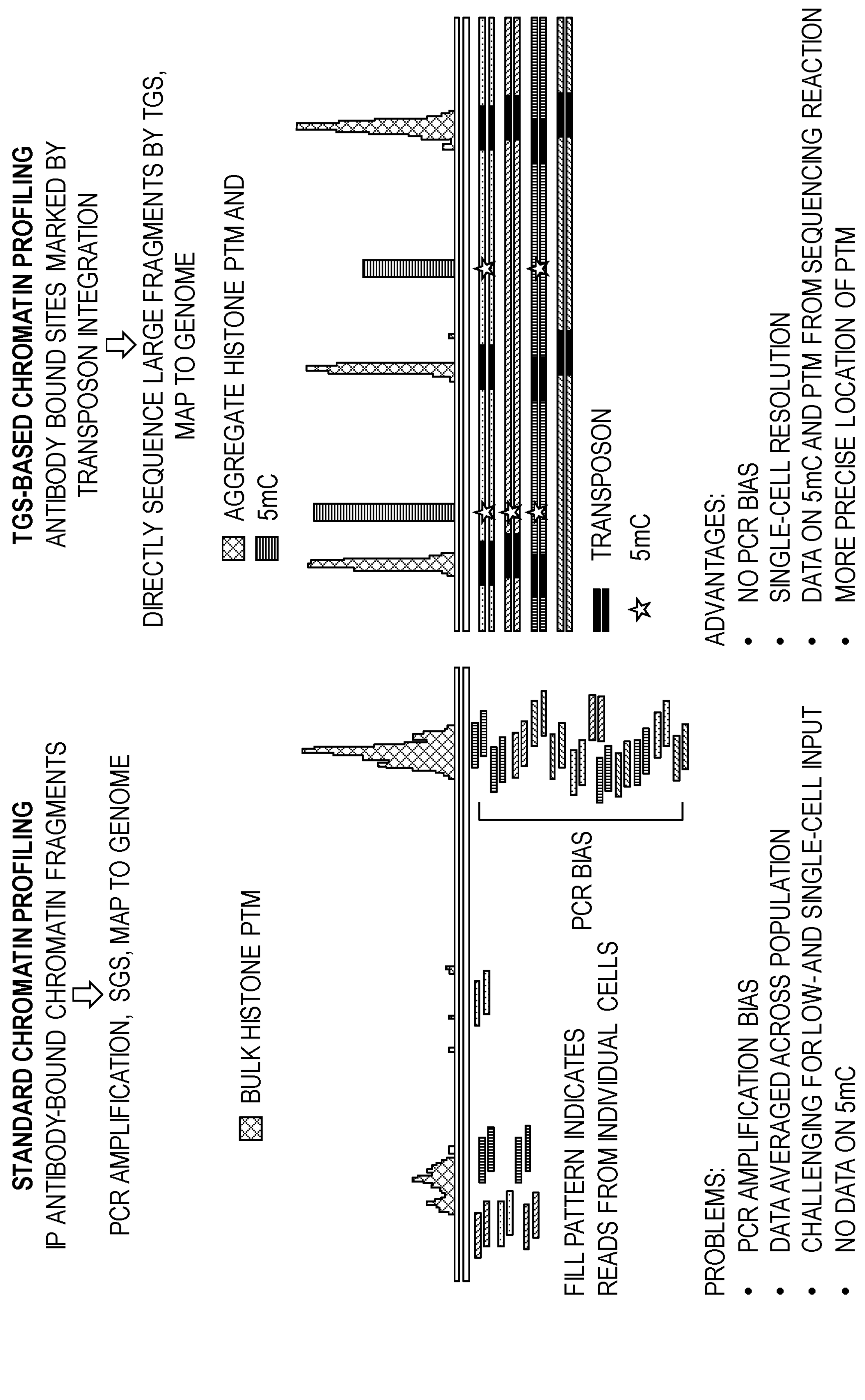
FIG. 4 shows the advantages of chromatin profiling using TGS vs. current SGS approaches (i.e. CUT&Tag, ChIP-seq).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of nucleosomes, and transiently and stably transfected cells. Such techniques are known to those skilled in the art. See, e.g., SAMBROOK et al., MOLECULAR CLONING: A LABORATORY MANUAL 4th Ed. (Cold Spring Harbor, NY, 2012); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid, protein means that the nucleic acid or protein does not contain any element other than the recited element(s) that significantly alters (e.g., more than about 1%, 5% or 10%) the function of interest of the nucleic acid or protein.

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By "substantially retain" a property, it is meant that at least about 75%, 85%, 90%, 95%, 97%, 98%, 99% or 100% of the property (e.g., activity or other measurable characteristic) is retained.

The term "synthetic" refers to a compound, molecule, or complex that does not exist in nature.

The term "DNA barcode" refers to a nucleic acid sequence that can be used to unambiguously identify a DNA molecule in which it is located. The length of the barcode determines how many unique sequences can be present in a library. For example, a 1 nucleotide (nt) barcode can code for 4 library members, a 2 nt barcode 16 variants, 3 nt barcode 64 variants, 4 nt 256 variants, 5 nt 1,024 variants and so on. The barcode(s) can be single-stranded (ss) DNA or double-stranded (ds) DNA or a combination thereof.

A first aspect of the invention relates to a synthetic transposon comprising, consisting essentially of, or consisting of a DNA barcode region linked on its 5' and 3' end to a flanking region that is recognized by a transposase, wherein the synthetic transposon does not encode a transposase. A flanking region that is "recognized" by a transposase is one that is specifically bound by a cognate transposase and functions to insert the transposon into DNA. In some embodiments, the flanking region is identical to or derived from one found in a naturally-occurring DNA transposon, such as the 19 bp Mosaic Ends (ME) of Tn5. In some embodiments, the flanking region may have a length of 7-40 nucleotides, e.g., 7, 8, 9, 10, 11, 12, 13, 14, 15, 16, 17, 18, 19, 20, 22, 24, 26, 28, 30, 32, 34, 36, 38, or 40 nucleotides or any range therein. In some embodiments, the flanking regions comprise terminal inverted repeats flanked by a short direct repeat. In some embodiments, the flanking region comprises a DNA barcode. The DNA barcode may have a length of less than 400, 300, 200, or 50 nucleotides. In some embodiments, the DNA barcode may have a length of at least 6, 7, 8, 9, 10, 12, 14, 16, 18, 20, 22, 24, 26, 28, or 30 nucleotides. In some embodiments, one or more of the nucleotides in the flanking region may be modified, e.g., by methylation or labeling, e.g., with biotin.

Another aspect of the invention relates to a transposome comprising the synthetic transposon of the invention and a transposase bound to each of the terminal inverted repeats. In some embodiments, the transposase may be a wild-type transposase, e.g., Tn5, Mu, IS5, IS91, Tn552, Ty1, Tn7, Tn/O, Mariner, P Element, Tn3, Tn10, or Tn903. In some embodiments, the transposase is modified from a wild-type transposase, e.g., a mutated hyperactive transposase. Such modified transposases are known in the art. In some embodiments, the transposase is Tn5 or a modified Tn5, e.g., a hyperactive Tn5 comprising one or more of the mutations E54K, M56A, or L372P.

A further aspect of the invention relates to a library comprising two or more of the synthetic transposon of invention and/or two or more of the transposome of the invention, wherein each synthetic transposon comprises a unique DNA barcode. In some embodiments, the library may comprise 5, 10, 50, 100, 250, 500, 1000, 5000 or more transposons and/or transposomes, each with a unique DNA barcode.

An additional aspect of the invention relates to a kit comprising the synthetic transposon, transposome, and/or the library of the invention. In some embodiments, the kit further comprises one or more transposases that recognize the sequence of the synthetic transposon. The kit may further comprise additional components for carrying out the methods of the invention, including but not limited to enzymes, antibodies, nucleotides, beads, buffers, containers, instructions, etc. Another aspect of the invention relates to a method for chromatin mapping, comprising:

a) targeting an enzyme to a specific feature in chromatin in a sample;
b) activating the enzyme to alter or label DNA local to the feature;
c) preparing the chromatin for sequencing;
d) sequencing the chromatin using long-read sequencing; and
e) mapping the location of the chromatin feature based on the locations of altered or labeled DNA.

The chromatin to be mapped in the assays of the invention may be from any source, including organs, tissues, cells, or cell-free. The amount of chromatin to be used may vary widely due to the sensitivity of the assay. In some embodiments, the sample comprises chromatin from less than 1000, 500, 100, 10, or 5 cells. In some embodiments, the sample comprises chromatin from 1 cell.

The methods of the invention can be carried out on any scale depending on the size of the sample. In some embodiments, the steps are carried out in a well of a multiwall plate. In some embodiments, the steps are carries out on a single cell scale, e.g., using a single cell droplet-based method or combinatorial indexing method.

The sample comprising the chromatin to be mapped in the assays of the invention may comprise cells or nuclei comprising the chromatin. In some embodiments, the cells or nuclei are attached to a solid support for ease of manipulation during the steps of the method. The solid support may be, without limitation, a well or a bead, e.g., a magnetic bead. In some embodiments, the cell or nuclei are not attached to a solid support.

In some embodiments, the cells or nuclei are permeabilized to enhance access of components to the chromatin. For example, cells can be permeabilized with digitonin, e.g., about 0.01% digitonin. In some embodiments, the cells or nuclei are not permeabilized.

In some embodiments, the sample comprises chromatin that has been isolated from cells or nuclei.

The sample comprising chromatin to be mapped may be from any source. In some embodiments, the chromatin is obtained from a biological sample. The biological sample may be, without limitation, blood, serum, plasma, urine, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, lymphatic fluid, or cerebrospinal fluid.

In some embodiments, the chromatin is from a diseased tissue or sample. In some embodiments, the chromatin is from non-diseased tissue or sample. In some embodiments, the chromatin is from a peripheral tissue or cell, e.g., a peripheral blood mononuclear cell.

In some embodiments, the chromatin is from cultured cells, e.g., a cell line or primary cells. In some embodiments, the chromatin is from an animal model of a disease or disorder. In some embodiments, the chromatin is from a subject, e.g., a patient, having or suspected of having a disease or disorder.

The methods of the invention can be used to perform any type of chromatin mapping, e.g., mapping any kind of specific feature of interest, including but not limited to genomic location and abundance of chromatin modifications, chromatin associated proteins (ChAPs), chromatin accessibility, and nucleosome positioning.

In one aspect, the methods of the invention include a method for mapping chromatin accessibility. The enzyme used in the mapping of chromatin accessibility may be any enzyme capable of detectably altering or labeling DNA where it is accessible. In one embodiment, the enzyme is an integrase or a DNA methyl transferase. In one embodiment, the enzyme used in the mapping of chromatin accessibility is a transposase. In some embodiments, the transposase may be a wild-type transposase, e.g., Tn5, Mu, IS5, IS91, Tn552, Ty1, Tn7, Tn/O, Mariner, P Element, Tn3, Tn10, or Tn903. In some embodiments, the transposase is modified from a wild-type transposase, e.g., a mutated hyperactive transposase. Such modified transposases are known in the art. In some embodiments, the transposase is Tn5 or a modified Tn5.

In some embodiments, the method comprises contacting a sample comprising chromatin with the synthetic transposon, transposome, or library of the invention under conditions in which the synthetic transposon can be inserted into the chromatin.

In some embodiments, the activating of the enzyme in step b) comprises adding a factor necessary for enzyme activity, e.g., by adding an ion such as calcium or magnesium. Once activated, the enzyme alters or labels DNA local to the feature. The term "local" in this context refers to DNA within 5-30 nucleotides (e.g., 5, 6, 7, 8, 9, 10, 11, 12, 13, 14, 15, 16, 17, 18, 19, 20, 21, 22, 23, 24, 25, 26, 27, 28, 29, or 30 nucleotides or any range therein, e.g., less than 6, 7, 8, 9, 10, 11, 12, 13, 14, 15, 16, 17, 18, 19, 20, 21, 22, 23, 24, 25, 26, 27, 28, 29, or 30 nucleotides) or 3-18 nm (e.g., 3, 4, 5, 6, 7, 8, 9, 10, 11, 12, 13, 14, 15, 16, 17, or 18 nm or any range therein, e.g., less than 4, 5, 6, 7, 8, 9, 10, 11, 12, 13, 14, 15, 16, 17, or 18 nm) of the feature.

In some embodiments, the method further comprises repairing transposon ligation sites prior to sequencing, e.g., using a DNA polymerase such as DNA polymerase I and a DNA ligase such as T4 DNA ligase.

In some embodiments of the method of mapping chromatin accessibility, two or more samples are contacted with a synthetic transposon and each sample is contacted with a different synthetic transposon comprising a unique DNA barcode. In some embodiments, 2, 3, 4, 5, 6, 7, 8, 9, 10, 15, 20, 25, 50, 100, 250, 500, or 1000 or more samples are each contacted with a different synthetic transposon comprising a unique DNA barcode. In some embodiments, the two or more samples may be pooled after step b).

In one aspect, the methods of the invention include a method for mapping chromatin modifications, chromatin-associated proteins, or nucleosome positioning. In some embodiments, the chromatin modification is a histone modification (e.g., a post-translational modification), histone variant, or a DNA modification (e.g., a post-transcriptional modification).

The histone PTM may be any PTM for which measurement is desirable. In some embodiments, the histone PTM is, without limitation, N-acetylation of serine and alanine; phosphorylation of serine, threonine and tyrosine; N-crotonylation, N-acylation of lysine; N6-methylation, N6,N6-dimethylation, N6,N6,N6-trimethylation of lysine; omega-N-methylation, symmetrical-dimethylation, asymmetrical-dimethylation of arginine; citrullination of arginine; ubiquitinylation of lysine; sumoylation of lysine; O-methylation of serine and threonine, ADP-ribosylation of arginine, aspartic acid and glutamic acid, or any combination thereof.

Several naturally occurring histone variants are known in the art and any one or more of them may be included in a nucleosome. Histone variants include, without limitation, H3.3, H2A.Bbd, H2A.Z.1, H2A.Z.2, H2A.X, mH2A1.1, mH2A1.2, mH2A2, TH2B, or any combination thereof.

The DNA post-transcriptional modification may be any modification for which measurement is desirable. In some embodiments, the DNA post-transcriptional modification is 5-methylcytosine, 5-hydroxymethylcytosine, 5-formylcytosine, 5-carboxylcytosine, 3-methylcytosine, or any combination thereof.

The chromatin-associated protein may be any chromatin-associated protein for which measurement is desirable. In some embodiments, the chromatin-associated protein is a transcription factor, a histone binding protein, or a DNA binding protein.

In methods for mapping chromatin modifications, chromatin-associated proteins, or nucleosome positioning, the step of targeting an enzyme to a specific feature in chromatin in a sample comprises contacting the chromatin with an antibody, aptamer, or recognition agent that specifically binds to the feature. The antibody, aptamer, or recognition agent used in the methods of the invention may be any agent that specifically recognizes and binds to a target, e.g., an antigen. The term "antibody" includes antigen-binding fragments thereof, such as scFv, Fab, Fv, Fab', $F(ab')_2$ fragments, dAb, VHH, nanobodies, V(NAR) or minimal recognition units.

For methods of mapping chromatin modifications, chromatin-associated proteins, or nucleosome positioning, the enzyme is linked to a protein that binds the antibody, aptamer, or recognition agent, e.g., an antibody binding protein. In some embodiments, the antibody-binding protein may be, without limitation, protein A, protein G, a fusion between protein A and protein G, protein L, or protein Y.

The enzyme used in the mapping of mapping chromatin modifications, chromatin-associated proteins, or nucleosome positioning may be any enzyme capable of detectably altering or labeling DNA where it is accessible. In one embodiment, the enzyme is an integrase or a DNA methyl transferase. In one embodiment, the enzyme used in the mapping of chromatin accessibility is a transposase. In some embodiments, the transposase may be a wild-type transposase, e.g., Tn5, Mu, IS5, IS91, Tn552, Ty1, Tn7, Tn/O, Mariner, P Element, Tn3, Tn10, or Tn903. In some embodiments, the transposase is modified from a wild-type transposase, e.g., a mutated hyperactive transposase. Such modified transposases are known in the art. In some embodiments, the transposase is Tn5 or a modified Tn5.

In some embodiments, the method comprises contacting a sample comprising chromatin with the synthetic transposon, transposome, or library of the invention under conditions in which the synthetic transposon can be inserted into the chromatin.

In some embodiments, the activating of the enzyme in step b) comprises adding a factor necessary for enzyme activity, e.g., by adding an ion such as calcium or magnesium.

In some embodiments, the method further comprises repairing transposon ligation sites prior to sequencing, e.g., using a DNA polymerase such as DNA polymerase I and a DNA ligase such as T4 DNA ligase.

In some embodiments of the method of mapping chromatin modifications, chromatin-associated proteins, or nucleosome positioning, two or more samples are contacted with a synthetic transposon and each sample is contacted with a different synthetic transposon comprising a unique DNA barcode. In some embodiments, 2, 3, 4, 5, 6, 7, 8, 9, 10, 15, 20, 25, 50, 100, 250, 500, or 1000 or more samples are each contacted with a different synthetic transposon comprising a unique DNA barcode. In some embodiments, the two or more samples may be pooled after step b).

For all of the methods of the invention, the methods may be carried out using a combinatorial cellular indexing technique. In some embodiments, the method may be carried out on a population of cells and step c) comprises dividing the population of cells into groups and processing the cells for sequencing using adaptors that include a second barcode or PCR amplification using primers that include a second barcode so that each cell comprises a double barcode signature. In some embodiments, each group of cells may comprise less than about 1000, 500, 250, 100, or 50 cells, e.g., about 10 to about 30 cells, e.g., about 20 cells.

For all of the methods of the invention, the methods may be carried out as part of a multiomic process wherein additional analyses are performed on the same samples, e.g., based on the long-read sequencing information. In some embodiments, the methods further comprise analyzing a DNA modification in the chromatin, e.g., DNA methylation.

As defined herein "long-read sequencing" refers to third generation sequencing techniques that work on the single molecule level and provide sequence reads of at least 10 kb, e.g., at least 50 kb or 100 kb. The long-read sequencing may be carried out by any method known in the art. In some embodiments, the long-read sequencing comprises nanopore sequencing, such as techniques available from OXFORD NANOPORE TECHNOLOGIES® (ONT). In some embodiments, the long-read sequencing comprises single molecule real time sequencing, such as techniques available from Pacific BioSciences®.

In some embodiments of the methods of the invention, the methods may further comprise a step of mechanically or enzymatically shearing the sample prior to sequencing. In other embodiments, no shearing occurs prior to sequencing.

In some embodiments of the methods of the invention, the methods may further comprise a step of amplifying the sample prior to sequencing. In other embodiments, no amplifying occurs prior to sequencing, enabling analysis of native DNA modifications.

The results obtained from the methods of the invention may be used for any purpose where information on chromatin structure and/or modification, e.g., epigenetic changes, would be useful. In some embodiments, the methods may further comprise the step of using the sequencing results to compare chromatin features between healthy and disease tissues. In some embodiments, the methods may further comprise the step of using the sequencing results to predict a disease state. In some embodiments, the methods may further comprise the step of using the sequencing results to monitor response to therapy. In some embodiments, the methods may further comprise the step of using the sequencing results to analyze tumor heterogeneity.

The methods of the invention may be used for detecting and quantitating the presence of an epigenetic modification in chromatin. An antibody, aptamer, or recognition agent that specifically binds to the epigenetic modification may be used to detect and quantitate the chromatin element or modification at various genomic loci.

The methods of the invention may be used for determining and quantitating the epigenetic status of chromatin in a subject having a disease or disorder. An antibody, aptamer, or recognition agent that specifically binds to one or more epigenetic modifications that may be associated with the disease or disorder of the subject may be used to detect and quantitate the chromatin element or modification at various genomic loci. By this method, one can determine if a subject having a disease or disorder, e.g., a tumor, has an epigenetic modification that is known to be associated with the tumor type.

The methods of the invention may be used for monitoring changes in epigenetic status of chromatin over time in a subject. This method may be used to determine if the epigenetic status is improving, stable, or worsening over time. The steps of the method may be repeated as many times as desired to monitor changes in the status of an epigenetic modification, e.g., 2, 3, 4, 5, 6, 7, 8, 9, 10, 25, 50, or 100 or more times. The method may be repeated on a regular schedule (e.g., daily, weekly, monthly, yearly) or on an as needed basis. The method may be repeated, for example, before, during, and/or after therapeutic treatment of a subject; after diagnosis of a disease or disorder in a subject; as part of determining a diagnosis of a disease or disorder in a subject; after identification of a subject as being at risk for development of a disease or disorder; or any other situation where it is desirable to monitor possible changes in the chromatin element or modification at various genomic loci.

The methods of the invention may be used for measuring on-target activity of an epigenetic-targeting drug. The methods may be carried out before, during, and/or after administration of an epigenetic-targeting drug to determine the capability of the drug to alter the epigenetic status of the subject.

The methods of the invention may be used for monitoring the effectiveness of an epigenetic therapy in a subject having a disease or disorder associated with epigenetic modifications.

Epigenetic therapies are those designed to alter the epigenetic status of proteins (e.g., histones) or DNA. One example of an epigenetic therapy includes lysine deacetylase inhibitors (formerly termed histone deacetylase inhibitors) (e.g., vorinostat (suberoylanilide hydroxamic acid), CI-994 (tacedinaline), MS-275 (entinostat), BMP-210, M344, NVP-LAQ824, LBH-529 (panobinostat), MGCD0103 (mocetinostat), PXD101 (belinostat), CBHA, PCI-24781, ITF2357, valproic acid, trichostatin A, and sodium butyrate), which are used to treat cutaneous T-cell lymphoma (CTCL) or in clinical trials for the treatment of hematologic and solid tumors, including lung, breast, pancreas, renal, and bladder cancers, melanoma, glioblastoma, leukemias, lymphomas, and multiple myeloma. A further example of an epigenetic therapy is histone acetyltransferase inhibitors (e.g., epigallocatechin-3-gallate, garcinol, anacardic acid, CPTH2, curcumin, MB-3, MG149, C646, and romidepsin). Another example of an epigenetic therapy is DNA methyltransferase inhibitors (e.g., azacytidine, decitabine, zebularine, caffeic acid, chlorogenic acid, epigallocatechin, hydralazine, procainamide, procaine, and RG108), which have been approved for treatment of acute myeloid leukemia, myelodysplastic syndrome, and chronic myelomonocytic leukemia and in clinical trials for treatment of solid tumors. Other epigenetic therapies include, without limitation, lysine methyltransferases (e.g., pinometostat, tazometostat, CPI-1205); lysine demethylases (e.g., ORY1001); arginine methyltransferases (e.g., EPZ020411); arginine deiminases (e.g., GSK484); and isocitrate dehydrogenases (e.g., enasidenib, ivosidenib). See Fischle et al., *ACS Chem. Biol.* 11:689 (2016); DeWoskin et al., *Nature Rev.* 12:661 (2013); Campbell et al., *J. Clin. Invest.* 124:64 (2014); and Brown et al., *Future Med. Chem.* 7:1901 (2015); each incorporated by reference herein in its entirety.

The steps of the method may be repeated as many times as desired to monitor effectiveness of the treatment, e.g., 2, 3, 4, 5, 6, 7, 8, 9, 10, 25, 50, or 100 or more times. The method may be repeated on a regular schedule (e.g., daily, weekly, monthly, yearly) or on as needed basis, e.g., until the therapeutic treatment is ended. The method may be repeated, for example, before, during, and/or after therapeutic treatment of a subject, e.g., after each administration of the treatment. In some embodiments, the treatment is continued until the method of the invention shows that the treatment has been effective.

The methods of the invention may be used for selecting a suitable treatment for a subject having a disease or disorder associated with epigenetic modifications based on the epigenetic status of chromatin in the subject.

The methods may be applied, for example, to subjects that have been diagnosed or are suspected of having a disease or disorder associated with epigenetic modifications. A determination of the epigenetic status of an epitope may indicate that the status of an epitope has been modified and an epigenetic therapy should be administered to the subject to correct the modification. Conversely, a determination that the status of an epitope has not been modified would indicate that an epigenetic therapy would not be expected to be effective and should be avoided. For example, a determination that a particular genomic locus has been acetylated or deacetylated may indicate that treatment with a histone deacetylase inhibitor would be appropriate. Similarly, a determination that a particular genomic locus has been hyper- or hypomethylated may indicate that treatment with a DNA methyltransferase inhibitor would be appropriate.

The methods of the invention may be used for determining a prognosis for a subject having a disease or disorder associated with epigenetic modifications based on the epigenetic status of chromatin in the subject.

In some instances, the epigenetic status of an epitope is indicative of the prognosis of a disease or disorder associated with epigenetic modifications. Thus, a determination of the epigenetic status of an epitope in a subject that has been diagnosed with or is suspected of having a disease or disorder associated with epigenetic modifications may be useful to determine the prognosis for the subject. Many such examples are known in the art. One example is prostate cancer and hypermethylation of the glutathione-S transferase P1 (GSTP1) gene promoter, the adenomatous polyposis *coli* (APC) gene, the genes PITX2, Clorf114, and GABRE~miR-452~miR-224, as well as the three-gene marker panel AOX1/Clorf114/HAPLN3 and the 13-gene marker panel GSTP1, GRASP, TMP4, KCNC2, TBX1, ZDHHC1, CAPG, RARRES2, SAC3D1, NKX2-1, FAM107A, SLC13A3, FILIPIL. Another example is prostate cancer and histone PTMs, including, without limitation, increased H3K18Acetylation and H3K4diMethylation associated with a significantly higher risk of prostate tumor recurrence, H4K12Acetylation and H4R3diMethylation correlated with tumor stage, and H3K9diMethylation associated with low-grade prostate cancer patients at risk for tumor recurrence. Another example is the link between overall survival in breast cancer patients and methylation status of CpGs in the genes CREB5, EXPH5, ZNF775, ADCY3, and ADMA8. Another example is glioblastoma and hypermethylation of intronic regions of genes like EGFR, PTEN, NF1, PIK3R1, RB1, PDGFRA, and QKI. A further example is inferior prognosis for colon cancer and methylation status of the promoter of the CNRIP1, FBN1, INA, MAL, SNCA, and SPG20 genes.

The methods of the invention may be used for identifying a biomarker of a disease or disorder associated with epigenetic modifications based on the epigenetic status of chromatin in a subject.

In this method, biological samples of diseased tissue may be taken from a number of patients have a disease or disorder and the epigenetic status of one or more epitopes determined. Correlations between the epitope status and the occurrence, stage, subtype, prognosis, etc., may then be identified using analytical techniques that are well known in the art.

In any of the methods of the invention, the disease or disorder associated with epigenetic modifications may be a cancer, a central nervous system (CNS) disorder, an autoimmune disorder, an inflammatory disorder, or an infectious disease.

The cancer may be any benign or malignant abnormal growth of cells, including but not limited to acoustic neuroma, acute granulocytic leukemia, acute lymphocytic leukemia, acute myelogenous leukemia, adenocarcinoma, adrenal carcinoma, adrenal cortex carcinoma, anal cancer, anaplastic astrocytoma, angiosarcoma, basal cell carcinoma, bile duct carcinoma, bladder cancer, brain cancer, breast cancer, bronchogenic carcinoma, cervical carcinoma, cervical hyperplasia, chordoma, choriocarcinoma, chronic granulocytic leukemia, chronic lymphocytic leukemia, chronic myelogenous leukemia, colon cancer, colorectal cancer, craniopharyngioma, cystadenosarcoma, embryonic carcinoma, endometrium cancer, endotheliosarcoma, ependymoma, epithelial carcinoma, esophageal carcinoma, essential thrombocytosis, Ewing's tumor, fibrosarcoma, genitourinary carcinoma, glioblastoma, glioma, gliosarcoma, hairy cell leukemia, head and neck cancer, hemangioblastoma, hepatic carcinoma, Hodgkin's disease, Kaposi's sarcoma, leiomyosarcoma, leukemia, liposarcoma, lung cancer, lymphangioendotheliosarcoma, lymphangiosarcoma, lymphoma, malignant carcinoid carcinoma, malignant hypercalcemia, malignant melanoma, malignant pancreatic insulinoma, mastocytoma, medullar carcinoma, medulloblastoma, melanoma, meningioma, mesothelioma, multiple myeloma, mycosis fungoides, myeloma, myxoma, myxosarcoma, neuroblastoma, non-Hodgkin's lymphoma, non-small cell lung carcinoma, oligodendroglioma, osteogenic sarcoma, ovarian cancer, pancreatic cancer, papillary adenosarcoma, papillary sarcoma, pinealoma, polycythemia vera, primary brain carcinoma, primary macroglobulinemia, prostate cancer, rectal cancer, renal cell carcinoma, retinoblastoma, rhabdomyosarcoma, sebaceous gland sarcoma, seminoma, skin cancer, small cell lung carcinoma, soft-tissue sarcoma, squamous cell carcinoma, stomach carcinoma, sweat gland carcinoma, synovioma, testicular carcinoma, throat cancer, thyroid carcinoma, and Wilms' tumor.

CNS disorders include genetic disorders, neurodegenerative disorders, psychiatric disorders, and tumors. Illustrative diseases of the CNS include, but are not limited to, Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder, mania, manic psychosis,), schizophrenia, schizoaffective disorder, schizophreniform disorder, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions, psychosis not otherwise specified (Psychosis NOS),), dementia, aging, paranoia, attention deficit disorder, psychosexual disorders, sleeping disorders, pain disorders, eating or weight disorders (e.g., obesity, cachexia, anorexia nervosa, and bulemia), ophthalmic disorders involving the retina, posterior tract, and optic nerve (e.g., retinitis pigmentosa, diabetic retinopathy and other retinal degenerative diseases, uveitis, age-related macular degeneration, glaucoma), and cancers and tumors (e.g., pituitary tumors) of the CNS.

Autoimmune and inflammatory diseases and disorders include, without limitation, myocarditis, postmyocardial infarction syndrome, postpericardiotomy syndrome, Subacute bacterial endocarditis, anti-glomerular basement membrane nephritis, interstitial cystitis, lupus nephritis, autoimmune hepatitis, primary biliary cirrhosis, primary sclerosing cholangitis, antisynthetase syndrome, sinusitis, periodontitis, atherosclerosis, dermatitis, allergy, allergic rhinitis, allergic airway inflammation, chronic obstructive pulmonary disease, eosinophilic pneumonia, eosinophilic esophagitis, hypereosinophilic syndrome, graft-versus-host disease, atopic dermatitis, tuberculosis, asthma, chronic peptic ulcer, alopecia areata, autoimmune angioedema, autoimmune progesterone dermatitis, autoimmune urticaria, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease, morphea, pemphigus vulgaris, pityriasis lichenoides et varioliformis acuta, Mucha-Habermann disease, psoriasis, systemic scleroderma, vitiligo, Addison's disease, autoimmune polyendocrine syndrome type 1, autoimmune polyendocrine syndrome type 2, autoimmune polyendocrine syndrome type 3, autoimmune pancreatitis, diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, celiac disease, Crohn's disease, irritable bowel syndrome, diverticulitis, microscopic colitis, ulcerative colitis, antiphospholipid syndrome, aplastic anemia, autoimmune hemolytic anemia, autoimmune lymphoproliferative syndrome, autoimmune neutropenia, autoimmune thrombocytopenia purpura, cold agglutinin disease, essential mixed cryoglobulinemia, Evans syndrome, pernicious anemia, pure red cell aplasia, thrombocytopenia, adiposis dolorosa, adult-onset Still's disease, ankylosing spondylitis, CREST syndrome, drug-induced lupus, enthesitisrelated arthritis, eosinophilic fasciitis, Felty syndrome, IgG4-related disease, juvenile arthritis, Lyme disease (chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, undifferentiated connective tissue disease, dermatomyositis, fibromyalgia, myositis, myasthenia gravis, neuromyotonia, paraneoplastic cerebellar degeneration, polymyositis, acute disseminated encephalomyelitis, acute motor axonal neuropathy, anti-N-methyl-D-aspartate receptor encephalitis, Balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, Oshtoran syndrome, pediatric autoimmune neuropsychiatric disorder associated with *Streptococcus* (PANDAS), progressive inflammatory neuropathy, restless leg syndrome, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease, Ménière's disease, Behçet's disease, eosinophilic granulomatosis with polyangiitis, giant cell arteritis, granulomatosis with polyangiitis, IgA vasculitis, Kawasaki's disease, leukocytoclastic vasculitis, lupus vasculitis, rheumatoid vasculitis, microscopic polyangiitis, polyarteritis nodosa, polymyalgia rheumatic, urticarial vasculitis, vasculitis, and primary immune deficiency.

The term "infectious diseases," as used herein, refers to any disease associated with infection by an infectious agent. Examples of infectious agents include, without limitation, viruses and microorganisms (e.g., bacteria, parasites, protozoans, cryptosporidiums). Viruses include, without limitation, Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV) and human T lymphotropic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B-19; Arenaviridae including Lassa virus; Orthomyxoviridae including influenza viruses; Poxviridae including Orf virus, molluscum contageosum virus, smallpox virus and Monkey pox virus; Togaviridae including Venezuelan equine encephalitis virus; Coronaviridae including corona viruses such as the severe acute respiratory syndrome (SARS) virus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus, TGE virus (swine), Foot and mouth disease virus, simian virus 5, human parainfluenza virus type 2, human metapneuomovirus, enteroviruses, and any other pathogenic virus now known or later identified (see, e.g., *Fundamental Virology*, Fields et al., Eds., 3rd ed., Lippincott-Raven, New York, 1996, the entire contents of which are incorporated by reference herein for the teachings of pathogenic viruses).

Pathogenic microorganisms include, but are not limited to, *Rickettsia, Chlamydia, Chlamydophila*, Mycobacteria, Clostridia, Corynebacteria, *Mycoplasma, Ureaplasma, Legionella, Shigella, Salmonella*, pathogenic *Escherichia coli* species, Bordatella, *Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4th ed., Lippincott, New York, 1990, the entire contents of which are incorporated herein by reference for the teachings of pathogenic microorganisms). Specific examples of microorganisms include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis* (*Yersinia pestis*), *Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza, Listeria monocytogenes, Shigella flexneri, Anaplasma phagocytophilum*, enterotoxic *Escherichia coli*, and *Schistosoma haematobium*.

In some embodiments, the disease or disorder includes, but is not limited to, obesity, diabetes, heart disease, autism, fragile X syndrome, ATR-X syndrome, Angelman syndrome, Prader-Willi syndrome, Beckwith Wiedemann syndrome, Rett syndrome, Rubinstein-Taybi syndrome, Coffin-Lowry syndrome Immunodeficiency-centrometric instability-facial anomalies syndrome, α-thalassaemia, leukemia, Cornelia de Langue syndrome, Kabuki syndrome, progressive systemic sclerosis, and cardiac hypertrophy.

Having described the present invention, the same will be explained in greater detail in the following examples, which are included herein for illustration purposes only, and which are not intended to be limiting to the invention.

EXAMPLES

Example 1: Chromatin accessibility assays using long-read sequencing

This example describes a protocol for carrying out a chromatin accessibility assay using the present invention.

Part I: ConA Bead Activation

1. Gently resuspend the ConA beads (Concanavalin A) and transfer 11 μl/sample to 1.5 ml tube for batch processing.
2. Place the tube on a magnet until slurry clears and pipet to remove supernatant (supe).
3. Add 100 μl/sample cold Bead Activation Buffer and pipet to mix. Place the tube on a magnet until slurry clears and pipet to remove supe.
4. Repeat previous step for total of two washes.

5. Resuspend beads in 11 μl/sample cold Bead Activation Buffer. Split activated ConA beads into separate tubes for different cell types and/or antibodies.
6. Aliquot 10 μl/sample of activated bead slurry into 8-strip tube. Keep beads on ice until needed.

Part II: Binding Cells to Activated Beads

7. Harvest 0.5 million cells/sample by spinning for 3 min at 600 g at room temperature (RT) in 1.5 ml tube, and decant supe.
8. Resuspend cells in 100 μl/sample RT Wash Buffer; spin for 3 min at 600 g at RT; decant supe.
9. Repeat previous step for total of two washes with Wash Buffer.
10. Resuspend cells in 100 μl/sample in RT Wash Buffer and aliquot 100 μl washed cells to each 8-strip tube containing 10 μl of activated bead. Gently vortex (setting #7) to mix.
11. Incubate cell: bead slurry for 10 min at RT (cells will adsorb to the activated ConA beads).
12. Place the tube on a magnet until slurry clears and pipet to remove supe.
13. While beads are on magnet, add 200 μl cold Wash Buffer directly onto beads of each sample, and then pipet to remove supe.
14. Repeat previous step for total of 2 washes and remove supe.
15. Add 50 μl cold Wash300 Buffer to each 8-strip tube, pipet to mix.

Part III: Binding of Barcoded pAG-mTn5

16. Add 2.5 μl barcoded pAG-mTn5 to each sample, and gently vortex.
17. Incubate samples for 1 hr at RT on nutator.
18. Chill tubes in magnet on ice until slurry clears and pipet to remove supe.
19. While beads are on magnet, add 200 μl cold Wash300 Buffer directly onto beads of each sample, and then pipet to remove supe.
20. Repeat previous step for total of 2 washes and remove supe.

Part IV: Targeted Chromatin Tagmentation

21. Add 5 μl cold TagMg10 Buffer to each sample, and pipet to mix.
22. Incubate 8-strip tube on thermocycler for 1 hr at 37° C.
23. Place the tube on a magnet until slurry clears and pipet to remove supe.
24. Add 5.5 μl TagStop Buffer Part V: DNA Repair and Ligation 25. Wash the sample using 100 μl of 0.2% SDS and then 1×PBS for total of 2 washes.
26. Centrifuge at 1000 g at 4° C. for 5 minutes and remove supe.
27. Incubate the sample in 10 U of DNA Polymerase I (NEB #M0209S) and 30 μM dNTPs in 200 μl of DNA Repair and Ligation Buffer at 37° C. for 2 hours.
28. Stop the reaction by adding 20 μl of 0.5 M EDTA and 2 μg of RNase A to the reaction and incubate for 30 min at 37° C.
29. Centrifuge at 1000 g at 4° C. for 5 minutes and remove supe.

Part VI: High MW genomic DNA purification for nanopore sequencing (using QIAGEN® Genomic-tips kit; cat #10223)

30. Add 1 ml of Buffer G2 to each sample, and pipet to mix.
31. Add 25 μl of QIAGEN® Protease stock solution (cat #19157), and incubate at 50° C. for 30-60 min.
32. Equilibrate a QIAGEN® Genomic-tip 20/G with 1 ml of Buffer QBT, and allow the QIAGEN® Genomictip to empty by gravity flow.
33. Vortex the sample for 10 sec at maximum speed and apply it to the equilibrated QIAGEN® Genomic-tip. Allow it to enter the resin by gravity flow.
34. Wash the QIAGEN® Genomic-tip with 3×1 ml of Buffer QC.
35. Elute the genomic DNA with 2×1 ml of Buffer QF (prewarm up to 50° C.).
36. Precipitate the DNA by adding 1.4 ml (0.7 volumes) room temperature isopropanol to the eluted DNA.
37. Mix and centrifuge immediately at 4300 g for at least 15 min at 4° C. Carefully remove the supe.
38. Wash the centrifuged DNA pellet with 1 ml of cold 70% ethanol. Vortex briefly and centrifuge at 4400 g for 10 min at 4° C. Carefully remove the supernatant without disturbing the pellet. Air-dry for 5-10 min.
39. Resuspend the DNA in 0.1-2 ml of 1 ml of sterile TE (10 mM Tris-HCl 1 mM EDTA, pH 8.0) on a platform shaker overnight at room temperature.

Part VII: Quality Control Check of DNA

40. Determine the purity of DNA using Nanodrop™. The OD260/280 ratio should be at least 1.8, and the OD260/230 should be between 2.0-2.2.
41. Determine average fragment size using the Agilent® 2100 Bioanalyzer and appropriate Bioanalyzer kit (e.g., Agilent DNA 7500 or 12000, cat #5067-1508).
42. Determine mass of DNA using Qubit® fluorimetry analysis (Invitrogen); should be at least 1 μg (or 100-200 fmol), if sequencing on MinION® OXFORD NANOPORE TECHNOLOGIES® sequencer.

Part VIII: Preparation of DNA Libraries for Nanopore Sequencing (Using OXFORD NANOPORE TECHNOLOGIES® Ligation Sequencing Kit; Cat #SQK-LSK109 and Protocol GDE_9063_v109_revQ_14Aug2019, and NEBNext® Companion Module for OXFORD NANOPORE TECHNOLOGIES® Ligation Sequencing; Cat #E7180S)

43. Transfer 1 mg DNA into a DNA LoBind tube, in a final volume of 50 ml nuclease-free water.
44. Perform end prep and DNA repair. Combine 47 ml DNA with DNA repair enzymes and buffers from the NEBNext Companion Module for OXFORD NANOPORE TECHNOLOGIES® Ligation Sequencing (cat #E7180S).
45. Purify DNA following end prep, using AMPure XP™ beads as described in the OXFORD NANOPORE TECHNOLOGIES® protocol (GDE_9063_v109_revQ_14Aug2019).
46. Quantify 1 μl of purified DNA using the Qubit fluorometer.
47. Perform adapter ligation. Combine 60 μl purified DNA with the Adaptor Mix (from the OXFORD NANOPORE TECHNOLOGIES® Ligation Sequencing Kit), T4 DNA Ligase (NEB) and buffer, as described in the OXFORD NANOPORE TECHNOLOGIES® protocol (GDE_9063_v109_revQ_14Aug2019).
48. Purify DNA following adapter ligation, using AMPure XP™ beads as described in the OXFORD NANOPORE TECHNOLOGIES® protocol (GDE_9063_v109_revQ_14Aug2019).
49. Quantify 1 μl of purified DNA using the Qubit fluorometer.

Part IX: Nanopore Sequencing, Using the OXFORD NANOPORE TECHNOLOGIES® MinION® Nanopore Sequencer (Note; could be Used with Other Oxford Nanopore Sequencers, Such as the PromethION® and GridION®).

50. Prepare flow cell: flush MinION® flow cell (R9.4.1) with a mixture of Flush Buffer and Flush Tether. Steps described in detail in in the OXFORD NANOPORE TECHNOLOGIES® protocol (GDE_9063_v109_revQ_14Aug2019).
51. Prepare Pre-Sequencing Mix, containing DNA library, sequencing buffer, and loading beads. For the R9.4.1 MinION® flow cell, OXFORD NANOPORE TECHNOLOGIES® recommends using 5-50 fmol of DNA in the sequencing library.
52. Load MinION® Flow Cell, per OXFORD NANOPORE TECHNOLOGIES® Manufacturing Instructions.
53. Start sequencing run: Connect MinION® to computer via a USB 3.0 port. Run MinION® sequencing reaction using MinKNOW® software, selecting kit (SQK-LSK109), "Fast" base-calling options, and setting the run length to 8 hours. Set output to FASTQ and FAST5 files. Note-Run length may change with type of flow cells, multiplexed samples, and other variations on the assay setup.

Part X: Bioinformatics Analysis

54. Transfer sequencing data to EPI2ME® software for bioinformatic analysis.
55. Map sequencing data to the human genome GRCh38 (or the most up-to-date reference genome) taking into account the inserted transposon/identifier sequence. Notably, the insertion of a transposon by pAG-mTn5 results in a 9 bp duplication on each side of the inserted transposon [31]. Thus, an algorithm that recognizes this identifier sequence and/or these duplicated sites allows the user to determine the site of transposition and the localization of PTMs on chromatin.

OXFORD NANOPORE TECHNOLOGIES® has published software specifically designed for barcode identification and deconvolution in nanopore sequencing data (i.e., Albacore), which will be utilized in the development of the bioinformatic pipeline.

Barcoded pAG-mTn5—Protein A/G fused hyperactive Tn5 loaded with barcoded transposon Buffers Bead Activation Buffer
- 20 mM HEPES, pH 7.9
- 10 mM KCl
- 1 mM $CaCl_2$
- 1 mM $MnCl_2$ Filter Sterilize Wash Buffer
- 20 mM HEPES, pH 7.5
- 150 mM NaCl
- 0.5 mM Spermidine
- 1× Roche Complete Protease Inhibitor-mini (CPI-mini), EDTA-free (Roche catalog #11836170001), 1 tab/10 ml
- Filter sterilize Wash300 Buffer
- 20 mM HEPES, pH 7.5
- 300 mM NaCl TagMg10 Buffer
- 20 mM HEPES pH 7.5, 300 mM NaCl
- 10 mM $MgCl_2$
- 0.5 M spermidine (0.5 µl/ml)
- 1× CPI-mini TagStop Buffer
- 10 mM TAPS, pH 8.5
- 0.03% SDS DNA Repair and Ligation Buffer
- 10 mM Tris-HCl
- 10 mM $MgCl_2$
- 50 mM NaCl
- 1 mM DTT Buffer G2
- 800 mM guanidine HCl
- 30 mM Tris·Cl, pH 8.0
- 30 mM EDTA, pH 8.0
- 5% Tween-20
- 0.5% Triton™ X-100

Buffer QBT (Equilibration Buffer)
- 750 mM NaCl
- 50 mM MOPS, pH 7.0
- 15% isopropanol
- 0.15% Triton™ X-100

Buffer QC (Wash Buffer)
- 1.0 M NaCl
- 50 mM MOPS, pH 7.0
- 15% isopropanol

Buffer QF (Elution Buffer)
- 1.25 M NaCl
- 50 mM Tris·Cl, pH 8.5
- 15% isopropanol

Example 2: Post-Translation Modification and Chromatin Associated Protein Assays Using Long-Read Sequencing Part I: ConA Bead Activation 1. Gently resuspend the ConA beads (Concanavalin A) and transfer 11 µl/sample to 1.5 ml tube for batch processing.
2. Place the tube on a magnet until slurry clears and pipet to remove supernatant (supe).
3. Add 100 µl/sample cold Bead Activation Buffer and pipet to mix. Place the tube on a magnet until slurry clears and pipet to remove supe.
4. Repeat previous step for total of two washes.
5. Resuspend beads in 11 µl/sample cold Bead Activation Buffer. Split activated ConA beads into separate tubes for different cell types and/or antibodies.
6. Aliquot 10 µl/sample of activated bead slurry into 8-strip tube. Keep beads on ice until needed.

Part II: Binding Cells to Activated Beads

7. Harvest 0.5 million cells/sample by spinning for 3 min at 600 g at room temperature (RT) in 1.5 ml tube, and decant supe.
8. Resuspend cells in 100 µl/sample RT Wash Buffer; spin for 3 min at 600 g at RT; decant supe.
9. Repeat previous step for total of two washes with Wash Buffer.
10. Resuspend cells in 100 µl/sample in RT Wash Buffer and aliquot 100 µl washed cells to each 8-strip tube containing 10 µl of activated bead. Gently vortex (setting #7) to mix.
11. Incubate cell: bead slurry for 10 min at RT (cells will adsorb to the activated ConA beads).

Part III: Binding of Primary Antibodies (PTMs or ChAPs)

12. Place the tube on a magnet until slurry clears and pipet to remove supe.
13. Add 50 µl cold Antibody Buffer to each sample and gently vortex.

14. Add 0.5 μl antibody to each sample and gently vortex.
15. Incubate 8-strip tube on nutator overnight at 4° C.

Part IV: Binding of Secondary Antibody

16. Place the tube on a magnet until slurry clears and pipet to remove supe.
17. Add 50 μl cold Wash Buffer to each sample and gently vortex.
18. Add 0.5 μl secondary antibody (1:100 dilution) to each sample and gently vortex.
19. Incubate 8-strip tube on nutator for 30 min at RT.
20. Place the tube on a magnet until slurry clears and pipet to remove supe.
21. While beads are on magnet, add 200 μl cold Wash Buffer directly onto beads of each sample, and then pipet to remove supe.
22. Repeat previous step for total of 2 washes and remove supe.
23. Add 50 μl cold Wash300 Buffer to each 8-strip tube, pipet to mix.

Part V: Binding of Barcoded pAG-mTn5

23. Add 2.5 μl barcoded pAG-mTn5 to each sample, and gently vortex.
24. Incubate samples for 1 hr at RT on nutator.
25. Chill tubes in magnet on ice until slurry clears and pipet to remove supe.
26. While beads are on magnet, add 200 μl cold Wash300 Buffer directly onto beads of each sample, and then pipet to remove supe.
27. Repeat previous step for total of 2 washes and remove supe.

Part VI: Targeted Chromatin Tagmentation

28. Add 50 μl cold TagMg10 Buffer to each sample, and pipet to mix.
29. Incubate 8-strip tube on thermocycler for 1 hr at 37° C.
30. Place the tube on a magnet until slurry clears and pipet to remove supe.
31. Add 5.5 μl TagStop Buffer Part VII: DNA Repair and Ligation 32. Wash the sample using 100 μl of 0.2% SDS and then 1×PBS for total of 2 washes.
33. Centrifuge at 1000 g at 4° C. for 5 minutes and remove supe.
34. Incubate the sample in 10 U of DNA Polymerase I (NEB #M0209S) and 30 μM dNTPs in 200 μl of DNA Repair and Ligation Buffer at 37° C. for 2 hours.
35. Stop the reaction by adding 20 μl of 0.5 M EDTA and 2 μg of RNase A to the reaction and incubate for 30 min at 37° C.
36. Centrifuge at 1000 g at 4° C. for 5 minutes and remove supe.

Part VIII: High MW Genomic DNA Purification for Nanopore Sequencing (Using QIAGEN® Genomic-Tips Kit; Cat #10223)

37. Add 1 ml of Buffer G2 to each sample, and pipet to mix.
38. Add 25 μl of QIAGEN® Protease stock solution (cat #19157), and incubate at 50° C. for 30-60 min.
39. Equilibrate a QIAGEN® Genomic-tip 20/G with 1 ml of Buffer QBT, and allow the QIAGEN® Genomictip to empty by gravity flow.
40. Vortex the sample for 10 sec at maximum speed and apply it to the equilibrated QIAGEN® Genomic-tip. Allow it to enter the resin by gravity flow.
41. Wash the QIAGEN® Genomic-tip with 3×1 ml of Buffer QC.
42. Elute the genomic DNA with 2×1 ml of Buffer QF (prewarm up to 50° C.).
43. Precipitate the DNA by adding 1.4 ml (0.7 volumes) room temperature isopropanol to the eluted DNA.
44. Mix and centrifuge immediately at 4300 g for at least 15 min at 4° C. Carefully remove the supe.
45. Wash the centrifuged DNA pellet with 1 ml of cold 70% ethanol. Vortex briefly and centrifuge at 4400 g for 10 min at 4° C. Carefully remove the supernatant without disturbing the pellet. Air-dry for 5-10 min.
46. Resuspend the DNA in 0.1-2 ml of 1 ml of sterile TE (10 mM Tris-HCl 1 mM EDTA, pH 8.0) on a platform shaker overnight at room temperature.

Part IX: Quality Control Check of DNA

47. Determine the purity of DNA using Nanodrop™. The OD260/280 ratio should be at least 1.8, and the OD260/230 should be between 2.0-2.2.
48. Determine average fragment size using the Agilent® 2100 Bioanalyzer and appropriate Bioanalyzer kit (e.g., Agilent DNA 7500 or 12000, cat #5067-1508).
49. Determine mass of DNA using Qubit® fluorimetry analysis (Invitrogen); should be at least 1 g (or 100-200 fmol), if sequencing on MinION® OXFORD NANOPORE TECHNOLOGIES® sequencer.

Part IX: Preparation of DNA Libraries for Nanopore Sequencing (Using OXFORD NANOPORE TECHNOLOGIES® Ligation Sequencing Kit; Cat #SQK-LSK109 and Protocol GDE_9063_v109_revQ_14Aug2019, and NEBNext® Companion Module for OXFORD NANOPORE TECHNOLOGIES® Ligation Sequencing; Cat #E7180S)

50. Transfer 1 μg DNA into a DNA LoBind tube, in a final volume of 50 μl nuclease-free water.
51. Perform End Prep and DNA Repair: Combine the following 47 μl DNA with DNA repair enzymes and buffers from the NEBNext Companion Module for OXFORD NANOPORE TECHNOLOGIES® Ligation Sequencing (cat #E7180S).
52. Purify DNA following end prep, using AMPure XP™ beads as described in the OXFORD NANOPORE TECHNOLOGIES® protocol (GDE_9063_v109_revQ_14Aug2019). 53. Quantify 1 μl of purified DNA using the Qubit fluorometer.
54. Perform Adapter Ligation: Combine 60 μl purified DNA with the Adaptor Mix (from the OXFORD NANOPORE TECHNOLOGIES® Ligation Sequencing Kit), T4 DNA Ligase (NEB) and buffer, as described in the OXFORD NANOPORE TECHNOLOGIES® protocol (GDE_9063_v109_revQ_14Aug2019).
55. Purify DNA following adapter ligation, using AMPure XP™ beads as described in the OXFORD NANOPORE TECHNOLOGIES® protocol (GDE_9063_v109_revQ_14Aug2019).
56. Quantify 1 μl of purified DNA using the Qubit fluorometer.

Part X: Nanopore Sequencing, Using g the OXFORD NANOPORE TECHNOLOGIES® MinION® Nanopore Sequencer (Note; could be Used with Other Oxford Nanopore Sequencers, Such as the PromethION® and GridION®).

57. Prepare flow cell: flush MinION® flow cell (R9.4.1) with a mixture of Flush Buffer and Flush Tether. Steps described in detail in in the OXFORD NANOPORE TECHNOLOGIES® protocol (GDE_9063_v109_revQ_14Aug2019).
58. Prepare Pre-Sequencing Mix, containing DNA library, sequencing buffer, and loading beads. For the R9.4.1

MinION® flow cell, OXFORD NANOPORE TECHNOLOGIES® recommends using 5-50fmol of DNA in the sequencing library.

59. Load MinION® Flow Cell, per OXFORD NANOPORE TECHNOLOGIES® Manufacturing Instructions.
60. Start sequencing run: Connect MinION® to computer via a USB 3.0 port. Run MinION® sequencing reaction using MinKNOW® software, selecting kit (SQK-LSK109), "Fast" base-calling options, and setting the run length to 8 hours. Set output to FASTQ and FAST5 files. Note-Run length may change with type of flow cells, multiplexed samples, and other variations on the assay setup.

Part XI: Bioinformatics Analysis

61. Transfer sequencing data to EPI2ME® software for bioinformatic analysis.
62. Map sequencing data to the human genome GRCh38 (or the most up-to-date reference genome) taking into account the inserted transposon/identifier sequence. Notably, the insertion of a transposon by pAG-mTn5 results in a 9 bp duplication on each side of the inserted transposon [31]. Thus, an algorithm that recognizes this identifier sequence and/or these duplicated sites allows the user to determine the site of transposition and the localization of PTMs on chromatin.

OXFORD NANOPORE TECHNOLOGIES® has published software specifically designed for barcode identification and deconvolution in nanopore sequencing data (i.e., Albacore), which will be utilized in the development of the bioinformatic pipeline.

Barcoded pAG-mTn5—Protein A/G fused hyperactive Tn5 loaded with barcoded transposon Buffers Bead Activation Buffer
- 20 mM HEPES, pH 7.9
- 10 mM KCl
- 1 mM $CaCl_2$
- 1 mM $MnCl_2$
- Filter sterilize Wash Buffer
- Wash Buffer+2 mM EDTA+0.01% digitonin Antibody Buffer
- 20 mM HEPES pH 7.5, 150 mM NaCl
- 2 mM EDTA
- 0.1% BSA
- 0.5 M spermidine (0.5 µl/ml)
- 1× CPI-mini Wash300 Buffer
- 20 mM HEPES, pH 7.5
- 300 mM NaCl TagMg10 Buffer
- 20 mM HEPES pH 7.5, 300 mM NaCl
- 10 mM $MgCl_2$
- 0.5 M spermidine (0.5 µl/ml)
- 1× CPI-mini TagStop Buffer
- 10 mM TAPS, pH 8.5
- 0.03% SDS DNA Repair and Ligation Buffer
- 10 mM Tris-HCl
- 10 mM $MgCl_2$
- 50 mM NaCl
- 1 mM DTT Buffer G2
- 800 mM guanidine HCl
- 30 mM Tris·Cl, pH 8.0
- 30 mM EDTA, pH 8.0
- 5% Tween-20
- 0.5% Triton™ X-100

Buffer QBT (Equilibration Buffer)
- 750 mM NaCl
- 50 mM MOPS, pH 7.0
- 15% isopropanol
- 0.15% Triton™ X-100

Buffer QC (Wash Buffer)
- 1.0 M NaCl
- 50 mM MOPS, pH 7.0
- 15% isopropanol

Buffer QF (Elution Buffer)
- 1.25 M NaCl
- 50 mM Tris·Cl, pH 8.5
- 15% isopropanol The foregoing examples are illustrative of the present invention and are not to be construed as limiting thereof. Although the invention has been described in detail with reference to preferred embodiments, variations and modifications exist within the scope and spirit of the invention as described and defined in the following claims.

REFERENCES

1. Skene, P. J., J. G. Henikoff, and S. Henikoff, *Targeted in situ genome-wide profiling with high efficiency for low cell numbers*. Nat Protoc, 2018. 13 (5): p. 1006-1019. (PubMed PMID: 29651053)
2. Skene, P. J. and S. Henikoff, *An efficient targeted nuclease strategy for high-resolution mapping of DNA binding sites*. Elife, 2017. 6. (PubMed PMID: 28079019) (PMC5310842)
3. van Steensel, B. and S. Henikoff, *Identification of in vivo DNA targets of chromatin proteins using tethered dam methyltransferase*. Nat Biotechnol, 2000. 18 (4): p. 424-8. (PubMed PMID: 10748524)
4. Ku, W. L., et al., *Single-cell chromatin immunocleavage sequencing (scChIC-seq) to profile histone modification*. Nat Methods, 2019. 16 (4): p. 323-325. (PubMed PMID: 30923384)
5. Schmid, M., T. Durussel, and U. K. Laemmli, *ChIC and ChEC; genomic mapping of chromatin proteins*. Mol Cell, 2004. 16 (1): p. 147-57. (PubMed PMID: 15469830)
6. Kaya-Okur, H. S., et al., *CUT&Tag for efficient epigenomic profiling of small samples and single cells*. Nat Commun, 2019. 10 (1): p. 1930. (PubMed PMID: 31036827) (PMC6488672)
7. Crawford, G. E., et al., *Genome-wide mapping of DNase hypersensitive sites using massively parallel signature sequencing (MPSS)*. Genome Res, 2006. 16 (1): p. 123-31. (PubMed PMID: 16344561) (PMC1356136)
8. Boyle, A. P., et al., *High-resolution mapping and characterization of open chromatin across the genome*. Cell, 2008. 132 (2): p. 311-22. (PubMed PMID: 18243105) (PMC2669738)
9 Schlesinger, F., et al., *De novo DNA demethylation and noncoding transcription define active intergenic regulatory elements*. Genome Res, 2013. 23 (10): p. 1601-14. (PubMed PMID: 23811145) (PMC3787258)
10. Jin, W., et al., *Genome-wide detection of DNase I hypersensitive sites in single cells and FFPE tissue samples*. Nature, 2015. 528 (7580): p. 142-6. (PubMed PMID: 26605532) (PMC4697938)
11. Giresi, P. G., et al., *FAIRE (Formaldehyde-Assisted Isolation of Regulatory Elements) isolates active regula-*

*tory elements from human chromatin*. Genome Res, 2007. 17 (6): p. 877-85. (PubMed PMID: 17179217) (PMC1891346)

12. Buenrostro, J. D., et al., *ATAC-seq: A Method for Assaying Chromatin Accessibility Genome-Wide*. Curr Protoc Mol Biol, 2015. 109: p. 21 29 1-9. (PubMed PMID: 25559105) (PMC4374986)
13. Buenrostro, J. D., et al., *Transposition of native chromatin for fast and sensitive epigenomic profiling of open chromatin, DNA-binding proteins and nucleosome position*. Nat Methods, 2013. 10 (12): p. 1213-8. (PubMed PMID: 24097267) (PMC3959825)
14. Ameur, A., W. P. Kloosterman, and M. S. Hestand, *Single-Molecule Sequencing: Towards Clinical Applications*. Trends Biotechnol, 2019. 37 (1): p. 72-85. (PubMed PMID: 30115375)
15. van Dijk, E. L., et al., *The Third Revolution in Sequencing Technology*. Trends Genet, 2018. 34 (9): p. 666-681. (PubMed PMID: 29941292)
16. Belser, C., et al., *Chromosome-scale assemblies of plant genomes using nanopore long reads and optical maps*. Nat Plants, 2018. 4 (11): p. 879-887. (PubMed PMID: 30390080)
17. Minervini, C. F., et al., *Mutational analysis in BCR-ABLI positive leukemia by deep sequencing based on nanopore MinION technology*. Exp Mol Pathol, 2017. 103 (1): p. 33-37. (PubMed PMID: 28663031)
18. Norris, A. L., et al., *Nanopore sequencing detects structural variants in cancer*. Cancer Biol Ther, 2016. 17 (3): p. 246-53. (PubMed PMID: 26787508) (PMC4848001)
19. Volden, R., et al., *Improving nanopore read accuracy with the R2C2 method enables the sequencing of highly multiplexed full-length single-cell cDNA*. Proc Natl Acad Sci USA, 2018. 115 (39): p. 9726-9731. (PubMed PMID: 30201725) (PMC6166824)
20. Byrne, A., et al., *Nanopore long-read RNAseq reveals widespread transcriptional variation among the surface receptors of individual B cells*. Nat Commun, 2017. 8: p. 16027. (PubMed PMID: 28722025) (PMC5524981)
21. Kurdyukov, S. and M. Bullock, *DNA Methylation Analysis: Choosing the Right Method*. Biology (Basel), 2016. 5 (1). (PubMed PMID: 26751487) (PMC4810160)
22. Ludwig, C. H. and L. Bintu, *Mapping chromatin modifications at the single cell level*. Development, 2019. 146 (12). (PubMed PMID: 31249006) (PMC6602357)
23. Euskirchen, P., et al., *Same-day genomic and epigenomic diagnosis of brain tumors using real-time nanopore sequencing*. Acta Neuropathol, 2017. 134 (5): p. 691-703. (PubMed PMID: 28638988) (PMC5645447)
24. Quick, J., et al., *Rapid draft sequencing and real-time nanopore sequencing in a hospital outbreak of Salmonella*. Genome Biol, 2015. 16: p. 114. (PubMed PMID: 26025440) (PMC4702336)
25. Quick, J., et al., *Real-time, portable genome sequencing for Ebola surveillance*. Nature, 2016. 530 (7589): p. 228-232. (PubMed PMID: 26840485) (PMC4817224)
26. Faria, N. R., et al., *Establishment and cryptic transmission of Zika virus in Brazil and the Americas*. Nature, 2017. 546 (7658): p. 406-410. (PubMed PMID: 28538727) (PMC5722632)
27. Rand, A. C., et al., *Mapping DNA methylation with high-throughput nanopore sequencing*. Nat Methods, 2017. 14 (4): p. 411-413. (PubMed PMID: 28218897) (PMC5704956)
28. Harada, A., et al., *A chromatin integration labelling method enables epigenomic profiling with lower input*. Nat Cell Biol, 2019. 21 (2): p. 287-296. (PubMed PMID: 30532068)
29. Cusanovich, D. A., et al., *Multiplex single cell profiling of chromatin accessibility by combinatorial cellular indexing*. Science, 2015. 348 (6237): p. 910-4. (PubMed PMID: 25953818) (PMC4836442)
30. Lareau, C. A., et al., *Droplet-based combinatorial indexing for massive-scale single-cell chromatin accessibility*. Nat Biotechnol, 2019. 37 (8): p. 916-924. (PubMed PMID: 31235917)
31. Reznikoff, W. S., *Transposon Tn5*. Annu Rev Genet, 2008. 42: p. 269-86. (PubMed PMID: 18680433)

What is claimed is:

1. A synthetic transposon comprising a DNA barcode region linked on its 5' end to a first flanking region and on its 3' end to a second flanking region, wherein each of the flanking regions comprises a terminal inverted repeat and is recognized by a transposase that is directly or indirectly targeted to a specific feature in chromatin, and wherein the synthetic transposon does not encode a transposase.

2. A transposome comprising the synthetic transposon of claim 1 and a transposase that is directly or indirectly targeted to a specific feature in chromatin bound to each of the terminal inverted repeats.

3. A library comprising two or more of the synthetic transposons of claim 1, wherein each synthetic transposon comprises a unique DNA barcode.

4. A kit comprising the synthetic transposon of claim 1.

5. A method for chromatin mapping, comprising:

a) directly or indirectly targeting an enzyme to a specific feature in chromatin in a sample;

b) activating the enzyme to non-destructively alter or label DNA within 5-30 nucleotides to the feature;

c) preparing the chromatin for sequencing;

d) sequencing the chromatin using long-read sequencing; and e) mapping a location of the chromatin feature based on the locations of altered or labeled DNA, wherein the enzyme is selected from the group consisting of transposase, integrase, and DNA methyl transferase.

6. The method of claim 5, wherein the sample comprises cells or nuclei.

7. The method of claim 6, wherein the cells or nuclei are attached to a solid support.

8. The method of claim 6, further comprising permeabilizing the cells or nuclei.

9. The method of claim 5, wherein the sample comprises chromatin isolated from cells.

10. The method of claim 5, wherein the method maps chromatin accessibility.

11. The method of claim 5, wherein the enzyme is a transposase.

12. The method of claim 5, wherein the enzyme is an integrase or a DNA methyl transferase.

13. The method of claim 5, wherein the method maps chromatin modifications, chromatin-associated proteins, chromatin accessibility, or nucleosome positioning.

14. The method of claim 5, wherein the enzyme is linked to an antibody binding protein.

15. The method of claim 13, wherein the enzyme is a transposase.

16. The method of claim 13, wherein the enzyme is an integrase or a DNA methyl transferase.

17. The method of claim 5, wherein the method is carried out on a population of cells and step c) comprises dividing the population of cells into groups and processing the cells for sequencing using adaptors that include a second barcode or PCR amplification using primers that include a second barcode so that each cell comprises a double barcode signature.

18. The method of claim 5, further comprising analyzing a DNA modification in the chromatin using a multiomic process.

19. The method of claim 18, wherein the DNA modification is methylation.

20. The method of claim 5, further comprising mechanically or enzymatically shearing the sample prior to sequencing.

* * * * *